(12) United States Patent
Heikkiläet al.

(10) Patent No.: US 6,846,657 B2
(45) Date of Patent: Jan. 25, 2005

(54) PROCESS FOR THE SIMULTANEOUS PRODUCTION OF XYLITOL AND ETHANOL

(75) Inventors: Heikki Heikkilä, Espoo (FI); Göran Hyöky, Kantvik (FI); Leena Rahkila, Espoo (FI); Marja Leena Sarkki, Kantvik (FI); Tapio Viljava, Kirkkonummi (FI)

(73) Assignee: Xyrofin Oy, Kotka (FI)

( * ) Notice: Subject to any disclaimer, the term of this patent is extended or adjusted under 35 U.S.C. 154(b) by 0 days.

(21) Appl. No.: 08/928,893

(22) Filed: Sep. 12, 1997

(65) Prior Publication Data

US 2003/0235881 A1 Dec. 25, 2003

Related U.S. Application Data

(63) Continuation of application No. 07/910,133, filed as application No. PCT/FI91/00011 on Jan. 10, 1991, now abandoned.

(30) Foreign Application Priority Data

Jan. 15, 1990 (FI) ................................. 900220

(51) Int. Cl.⁷ .............................. C12P 7/18; C12P 7/06; C12P 7/08; C12P 7/10; C12N 1/16
(52) U.S. Cl. ....................... 435/158; 435/105; 435/161; 435/163; 435/165; 435/255.4; 435/255.5; 435/255.7; 435/924; 435/938
(58) Field of Search ................................. 435/155, 161, 435/105, 255.2, 255.21, 158, 163, 165, 255.4, 255.5, 255.7, 924, 938, 164

(56) References Cited

U.S. PATENT DOCUMENTS

| | | | |
|---|---|---|---|
| 2,684,331 A | 7/1954 | Bauman | 210/24 |
| 2,911,362 A | 11/1959 | Wheaton | 210/31 |
| 2,985,589 A | 5/1961 | Broughton et al. | 210/34 |
| 3,586,537 A | 6/1971 | Steiner et al. | 127/37 |
| 3,619,369 A * | 11/1971 | Onishi | 435/158 |
| 3,627,637 A * | 12/1971 | Jaffe | 435/158 |
| 3,784,408 A | 1/1974 | Jaffe et al. | 127/37 |
| 3,928,193 A | 12/1975 | Melaja et al. | 210/31 |
| 4,008,285 A | 2/1977 | Melaja et al. | 260/635 |
| 4,066,711 A | 1/1978 | Melaja et al. | 260/637 |
| 4,075,406 A | 2/1978 | Melaja et al. | 536/1 |
| 4,096,036 A | 6/1978 | Liu et al. | 195/31 F |
| 4,368,268 A | 1/1983 | Gong | 435/161 |
| 4,471,114 A | 9/1984 | Sherman et al. | 536/127 |
| 4,631,129 A | 12/1986 | Heikkila | 210/635 |
| 4,857,642 A | 8/1989 | Kulprathipanja | 536/127 |
| 4,940,548 A | 7/1990 | Zinnen | 210/656 |
| 4,990,259 A | 2/1991 | Kearney et al. | 210/635 |
| 5,047,332 A * | 9/1991 | Chahal | 435/42 |
| 5,081,026 A * | 1/1992 | Heikkila et al. | 435/158 |
| 5,122,275 A | 6/1992 | Rasche | 210/659 |
| 5,127,957 A | 7/1992 | Heikkila et al. | 127/47 |
| 5,177,008 A | 1/1993 | Kampen | 435/139 |
| 5,198,120 A | 3/1993 | Masuda et al. | 210/659 |
| 5,225,580 A | 7/1993 | Zinnen | 554/30 |
| 5,637,225 A | 6/1997 | Heikkila et al. | 210/659 |
| 5,951,777 A | 9/1999 | Nurmi et al. | 127/61 |

FOREIGN PATENT DOCUMENTS

| | | |
|---|---|---|
| EP | 89109081.3 | 5/1987 |
| EP | 87119111.0 | 12/1987 |
| EP | 0 279 946 A3 | 8/1988 |
| EP | 0 279 946 A2 | 8/1988 |
| EP | 89109081.3 | 5/1989 |
| EP | 0 345 511 A2 | 12/1989 |
| EP | 0 345 511 A3 | 12/1989 |
| EP | 0 279 946 B1 | 8/1998 |
| EP | 0 345 511 B1 | 12/1999 |
| FR | 19890000209 | 1/1989 |
| FR | 2641545 | 7/1990 |
| FR | A1 2641545 | 7/1990 |
| JP | 62-235014 | 9/1987 |
| JP | 64-080409 | 3/1989 |
| WO | WO-A1-88/05467 | 7/1988 |
| WO | PCT/US89/05572 | 12/1989 |
| WO | PCT/FI90/00015 | 1/1990 |
| WO | WO 90/06796 | 6/1990 |
| WO | WO 90/08193 | 7/1990 |
| WO | 9008193 * | 7/1990 ................. 435/158 |
| WO | PCT/US90/07024 | 11/1990 |
| WO | WO 91/08815 | 6/1991 |

OTHER PUBLICATIONS

Jeffries, T.O. "Enzymatic Removal and Utilization of Hemi-cellulose from Pulps", *Abst–Pap–Am. Chem. Soc.,* 200meet, Pt1, Cell55, 1990.*

Lollmeier–Vogel, E. et al., "Shifting Product Formation From Xylitol to Ethanol In Pentox Fermentation with *Candida tropicalis* by Altering Environmental Parameters," *Ann. N.Y. Acad Sci,* vol. 434, pp 152–154, 1984.*

Chemical Abstracts, vol. 105, No. 5, Aug. 4, 1986, (Columbus, Ohio, US), J. C. Du Preez et al.: "Xylose fermentation by *Candida shehatae* and *Pichia stipitis*: effects of pH, temperatue and substrate concentration":, see p. 604, Abstract 41196y, & Enzyme Microb. Technol., 8 (6), 360–364 (1986).

Chemical Abstracts, vol. 112, No. 5, Jan. 29, 1990, (Columbus, Ohio, US), M.T.Amaral–Collaco et al.: Utilization of the hemicellulosic fraction of agro–Industrial residues by yeasts:, see p. 449, Abstract 34371t, & Enzyme Syst. Lignocellul Degrad., 221–230 (1989).

(List continued on next page.)

*Primary Examiner*—David M. Naff
(74) *Attorney, Agent, or Firm*—Kenyon & Kenyon

(57) ABSTRACT

The invention relates to a process for the simultaneous production of xylitol and ethanol from a hydrolyzed lignocellulose-containing material starting. The starting material is fermented with a yeast strain, the ethanol produced is recovered, a chromatographic separation is carried out on the remaining xylitol solution, and pure xylitol is crystallized.

24 Claims, 1 Drawing Sheet

OTHER PUBLICATIONS

Chemical Abstracts, vol. 114, No. 5, Feb. 4, 1991, (Columbus, Ohio, US), K.B. Taylor et al.: "The fermentation of xylose: studies by carbon–13 nuclear magnetic resonance spectroscopy", see p. 592, Abstract 41014y, & J. Ind. Microbiol., 6 (1), 29–41 (1990).

Chemical Abstract, vol. 98, No. 9, Feb. 28, 1983, (Columbus, Ohio, US), Gong, Cheng Shung et al.: Conversion of pentoses by yeasts:, see p. 484, Abstract 70314c, & Biotecnol. Bioeng., 25 (1), 85–102 (1983).

Publication: "Third European Congress On Biotechnology", by Weinheim presented in Muchen, Federal Republic of Germany, vol. II (Sep. 10–14, 1984).

Publication: "Chromatography of Oligosaccharides and Related Compounds on Ion–Exchange Resin" by Department of Engineering Chemistry, Chalmers University of Technology, Goteborg, Sweden, Advances in Chromatography, vol. 16, pp. 113–149 (1978).

Publication: "The Distribution of Polyalcohols Between Organic Ion Exchangers and Water" by Malte Mattisson and Olof Samuelson, Department of Engineering Chemistry, Chalmer Tekniska Hogskola, Goteborg, Sweden No. 7, pp. 1386–1394 (1958).

Publication: "Ion–Exchange Chromatography of Aldehydes, Ketones, Ethers, Alcohols, Polyols and Saccharids" published in Journal of Chromatographprinted by Chromatographic Reviews, Elsevier Scientific Publishing Company, Amsterdam–Printed in The Netherlands, 98 pp. 55–104 (1974).

Publication: "Xylitol dehydrogenase from Pachysolen tannophilus" by G. Ditzelmuller, C.P. Kubicek, W. Wohrer and M. Rohr of Institute for Biochemische Technologie and Mikrobiolgies, Wien, Austria, pp. 195–198 (Jul. 31, 1984).

Abstract: French Application No. FR19890000209 filed Jan. 10, 1989, Publication No. FR2641545 published Jul. 13, 1990 of Agrocinq pertains to a Process For The Biosynthesis of Xylitol.

Abstract: Japanese Application No. 62–235014 filed Aug. 21, 1987, Publication No. 64–080409 published Mar. 27, 1989 of Japan Organo Co., Ltd. pertains to a False Moving Bed Device.

Publication: "Fermentation of Cellulose and Hemicellulose Carbohydrates by Thermotolerant Yeasts" by Linda D. McCracken and Cheng–Shung Gong of Laboroatory of renewable Resources Engineering, A.A. Potter Engineering Center, Purdue University, West Lafayette, Indiana, published by Biotechnology and Bioengineering Symp. No. 12, 91–102 (1982).

Publication: "Conversion of D–Xylose Into Xylitol By Xylose Reductase From Candida Pelliculose Coupled With the Oxidoreductase System of Methanogen Strain HU" by V. Kitpreechavanich of Department of Microbiology, M. Hayasi, N. Nishio and S. Hagai of Department of Fermentation Technology, published Biotechnology Letter, vol. 6, No. 10, pp. 651–656 (1984).

Publication: "Quantitative Production of Xylitol From D–Xylose By A High–Xylitol Producing Yeast Mutant Candida tropicalis HXP2" by Cheng–Shung Gong, Li Fu Chen and George T. Tsao of Laboratory of Renewable Resources Engineering, A.A. Potter Engineering Center, Purdue University, West Lafayette, Indiana, published in Biotechnology Letters vol. 3 No. 3, pp. 130–135 (1981).

Publication: "Biotechnological Production of Xylitol. Part 3: Operation In Culture Media Made From Lignocellulose Hydrolysates", by Juan Carlos Parajo, Herminia Domiquez & Jose Manuel Dominguez of Department of Chemical Engineering, University of Vigo, Ourense, Spain, published by Bioresource Technology 66 (1998), pp. 25–40.

Publication: "Fermentation of Lignocellulosic Hydrolysates For Ethanol Production", by Lisbeth Olsson and Barbel Hanh Hagerdal of Applied Microbiology, University of Lund/Lund Institute of Technology, Lund Sweden, published by Enzyme and Microbial Technology 18: pp. 312–331, (1996).

Publication: "Alternative Sweeteners Second edition, revised and Expanded", by Albert Bar, Bioresco Ltd., Brussels, Belgium edited by Lyn O'Brien Nabors and Robert C. Gelardi of Calorie Control Council, Atlanta, Georgia, published by Marcel Dekker, Inc. pp. 349–379 (1991).

Abstract: Japanese Application No. 59–183571 filed Aug. 31, 1984, Publication No. 61–063291 (1063291), published Apr. 1, 1986 of Dai Ichi Kogyo Seiyaku Co., Ltd. pertains to the Production of Xylitol Through Enzymatic Process.

Abstract: Japanese Application No. 60–244968 filed Oct. 30, 1985, Publication No. 62–104588 (2104588), published May 15, 1987 of Nitto Electric Ind. Co., Ltd., pertains to Production of Xylitol.

Abstract: Japanese Application No. 59–1411 filed Jan. 10, 1984, Publication No. 60–145095 (0145095), published Jul. 31, 1995 of Jiyuujiyou Seishi KK, pertains to Preparation of Xylitol By Immobilized Microorganism.

Abstract: Japanese Publication No. 45–24834 (0024834), published Aug. 18, 1970 of Zaidan Hojin Noda Sangyak (Zaid), pertains to Production Of Xylitol By Fermentation.

J.C. Du Preez et al,: "Xylose fermentation by Candida shehatae and Pichia stipitis: effects of pH, temperature and substrate concentration", p. 604, abstrct 41196y** & Enzyme Microb. Technol. 1986 8(6), 360–364.

M.T. Amaral–Collaco et al.: "Utilization of the hemicellulosic fraction of agro–industrial residues by yeasts", Enzyme Syst. Lignocellul. Degrad. 1989, 221–230.

K.B. Taylor et al.: "The fermentation of xylose: studies by carbon13 nuclear magnetic resonance spectroscopy", J. Ind. Microbiol. 1990, 6 (1), 29–41.

Gong, Cheng Shung et al.: "Conversion of pentoses by yeasts", Biotechnol. Bioeng. 1983, 25 (1), 85–102.

International Search Report PCT/FI 91/00011, 1991.

Dofner, K., Ion Exchangers, Properties and Applications, Ann Arbor Science Publisher Inc., pp. 44–45.

Duolite C 464, Weak Acid Cation Exchange Resin, Feb. 1981, 3 pages.

Zaborsky, O., Immobilized Enzymes, CRC Press, pp. 5–27.

Sax, N. and Lewis, Sr., R., Hawley's Condensed Chemical Dictionary, 11th ed., pp. 15 and 893.

Morrison, R. and Boyd, R., Organic Chemistry, 5th ed., pp. 833 and 839.

Allenza, P., Scherl, D., and Detroy, R., Hydrolysis of Xylan by an Immobilized Xylanase from Aureobasidium pullulans, Biotechnology and Bioengineering Symp. No. 17 (1986) pp. 425–433.

Jenq, C.Y., Wang, S.S. and Davidson, B., Ultrafiltration of Raw Sewage Using an Immobilized Enzyme Membrane, Enzyme Microb. Technol., Apr. 1980, vol. 2, pp. 145–147.

Dekker, Robert F.H., Bioconversion of Hemicellulose: Aspects of Hemi–cellulase Production by *Trichoderma reesei* QM 9414 and Enzyme Saccharification of Hemicellulose, Abstract 177464d, Chemical Abstracts, vol. 98, 1983.

Weckstrom, L. and Leisola, M., Enzymatic Hydrolysis of Hemicellulose From Bisulfite Waste, Proc. Int. Ferment. Symp., 1981, vol. 2, pp. 21–26.

Poutanen, K. and Puls, J., Enzymatic Hydrolysis of Steam–Pretreated Lignocellulosic Materials, Third European Congress on Biotechnology, vol. II, Sep., 1984, pp. 217–223.

International Preliminary Examination Report for PCT/FI91/00011 and Official Action for FI 900220.

International Search Report for PCT/FI90/00015.

Hyrkas et al., Heran Laktoosin Hydrolyysi Immobilisoidulla β–Galaktosidaasilla, 1974, pp. 38–47 and English language summary and translation of abstract.

Horitsu H: Sugar Alcohol Prepn. by Treating Mixed Sugar Soln. Cong. Substrate Sugar and Hydrogen Donor Sugar with *Candida* Yeast, Dialog Information Services, File 351, WPI 81–90, Dialog Accession No. 88–297740/42.

Amaral–Collaco, et al., Utilization of the Hemicellulosic Fraction of Agro Industrial Residues by Yeasts, Abstract 34371t, Fermentations vol. 112, 1990.

Onishi et al., The Production of Xylitol, L–Arabinitol and Ribitol by Yeasts, Agr. Biol. Chem., vol. 30, No. 11, 1996, pp. 1139 and 1144.

Weckstrom, L. and Leisola, M., Enzymatic Hydrolysis of Hemicellulose From Bisulfite Waste, Abstract 96:124760z, Wood Products, vol. 96, 1982.

* cited by examiner

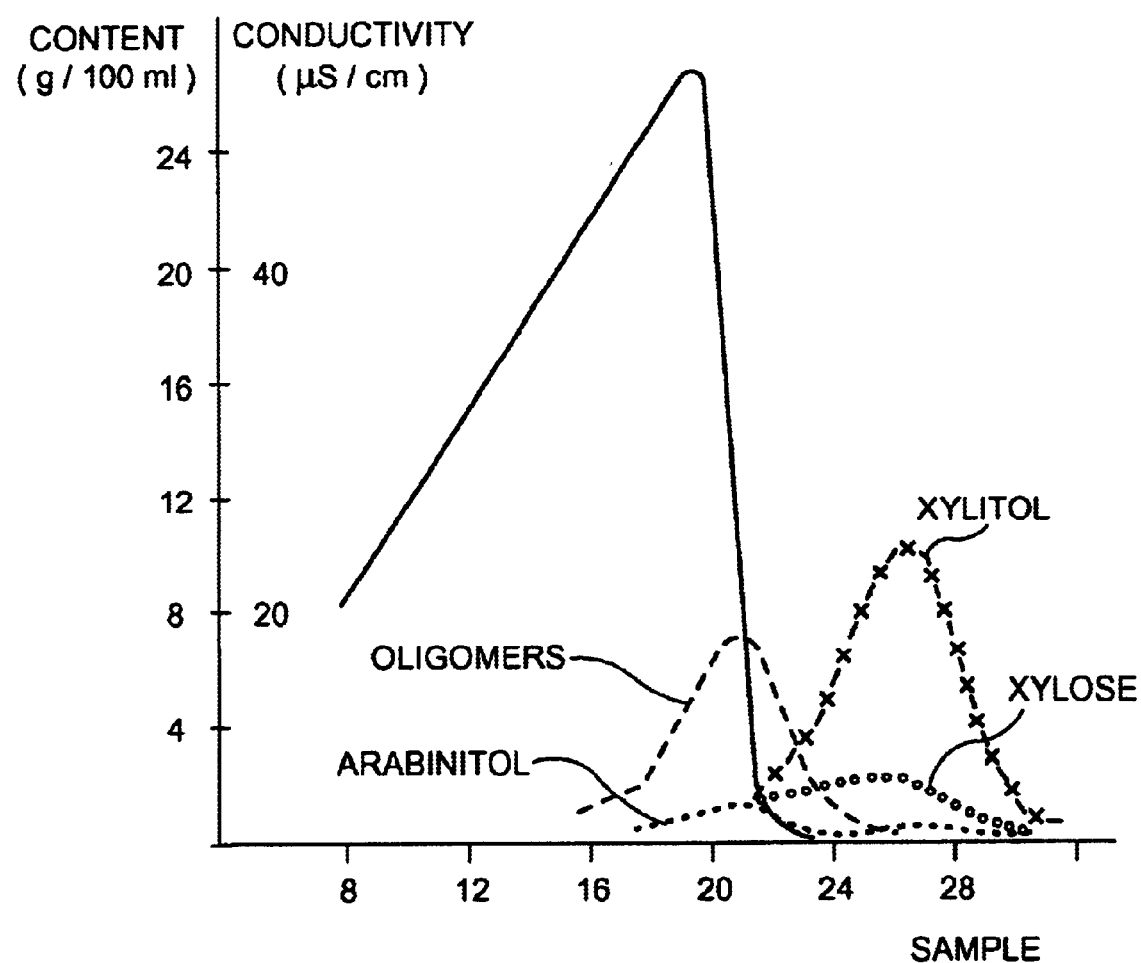

PROCESS FOR THE SIMULTANEOUS PRODUCTION OF XYLITOL AND ETHANOL

CROSS REFERNCES TO RELATED APPLICATIONS

This application is a continuation of U.S. Pat. No. U.S. Ser. No. 07/910,133 filed Jul. 14, 1993, now abandoned, which is a United States national stage application under 35 U.S.C. 371 of PCT International Application PCT/FI/00011, filed Jan. 10, 1991, which is based upon Finnish Patent Application No. 900220, filed on Jan. 15, 1990. This application is also commonly owned with Heikkila et al. U.S. Pat. No. 5,081,026, which issued on Jan. 14, 1992, from U.S. Ser. No. 611,385 filed Nov. 2, 1990 as provided under 35 USC §102 (e) and 35 USC §103(c).

The present invention relates to a process for the simultaneous production of xylitol and ethanol. A hydrolyzed lignocellulose-containing material is used as a starting material, and in accordance with the process the starting material is fermented with a yeast strain, whereafter the ethanol is recovered and a chromatographic separation is carried out on the fermented solution to obtain pure xylitol.

Xylitol is a naturally occurring sugar alcohol which is formed in the reduction reaction of xylose and which corresponds to "normal" sugar in sweetness and caloric content (4 kcal/g). Xylitol is found in small quantities in many fruits and vegetables and is also produced in the human body as a normal metabolic product. Xylitol is a very good special sweetener in different connections on account of its certain metabolic, dental and technical properties. It may be mentioned by way of example that xylitol metabolism is independent of the insulin metabolism, and therefore also diabetics can use xylitol. Xylitol also has a retarding effect on the bowel, wherefore it may have utility in reducing diets. Furthermore, it has been found that xylitol does not cause caries but has a cariostatic effect.

Despite the many advantages of xylitol, its use has been rather restricted. The reason for this is the relatively high price of xylitol, which in turn is a result of the difficulties of producing xylitol on a larger scale.

Ethanol is a well-known compound which has a wide use.

Xylitol has earlier been produced from xylane-containing materials by hydrolyzation, in which process a monosaccharide mixture containing e.g. xylose is obtained. Xylose is then converted to xylitol, generally in the presence of a nickel catalyst, such as Raney nickel. A number of processes for the production of xylose and/or xylitol from a xylane-containing material have been described in the literature in this field. As examples may be mentioned U.S. Pat. No. 3,784,408 (Jaffe et al.), U.S. Pat. No. 4,066,711 (Melaja et al.), U.S. Pat. No. 4,075,406 (Melaja et al.), U.S. Pat. No. 4,008,285 (Melaja et al.) and U.S. Pat. No. 3,586,537 (Steiner et al.).

These prior processes are all multi-step processes which are relatively costly and have inadequate efficiency. The greatest problems reside in the effective and total separation of xylose and/or xylitol from polyols and other hydrolysis by-products and the use of the by-products which are produced in large quantities in the process. The purification is very exacting for instance on account of the fact that the catalysts used in the reduction reaction of xylose are very sensitive. The purity of the final product for its part is greatly dependent on that the xylitol can be separated from the other products produced in the reduction reaction.

It is known that several yeast strains produce reductase enzymes which catalyze the reduction of sugars into corresponding sugar alcohols. Certain *Candida* strains have been reported to produce xylitol from xylose (Ditzelmuller, G. et al.: *FEMS Microbiology Letters* 25 (1985), pp. 195–198, Kitpreechavanich, M. et al.: *Biotechnology Letters* Vol. 6 (1984), pp. 651–656, Gong, C-S. et al.: *Biotechnology Letters* Vol. 3 (1981), pp. 125–130). However, these studies have been carried out on a laboratory scale only, and the literature in this field has not disclosed processes wherein crystalline pure xylitol is separated from the fermentation product.

U.S. application Ser. No. 611,383, filed Nov. 2, 1990, now U.S. Pat. No. 5,081,026, which is a continuation of U.S. application Ser. No. 297,791, filed Jan. 17, 1989, now abandoned. describes a process for the production of pure crystalline xylitol from plant material using chromatographic separation following hydrolysis and fermentation. However, in this process the majority of the raw material is lost as a worthless waste material. If a greater part of the raw materials could be converted to commercial products, this would essentially improve the economy of the overall process.

It is known that ethanol can be produced from cellulose and hemicellulose by fermenting with a suitable yeast strain. The production of ethanol from D-xylose has been described for instance in U.S. Pat. No. 4,368,268 (C-S. Gong), which publication particularly relates to the manufacturing of mutants which produce ethanol in high yields, and in *Biotechnology* and *Bioengineering Symp.* 12 (1982), pp. 91–102, McCracken, L. & Gong, C-S., wherein fermentation is performed with thermotolerant yeasts.

SUMMARY OF THE INVENTION

It has now been found that xylitol and ethanol can be produced simultaneously by using the process of the invention wherein xylose is converted to xylitol, while the majority of the other hexoses present in the raw material are converted to ethanol. Thus the raw material is effectively utilized and two commercially very important products are obtained in a pure form and with a high yield. The process is simple and effective.

The process of the invention is characterized in that the hydrolyzed starting material is fermented with a yeast strain, the ethanol produced is recovered, a chromatographic separation is carried out on the remaining xylitol solution, and pure xylitol is crystallized. Xylose-containing substances are used as starting materials, which in accordance with the invention are fermented with a yeast strain that is capable of converting xylose to xylitol and most hexoses to ethanol. By fermentation, a xylitol-rich solution is obtained wherefrom xylitol is recovered in a simple way. Laborious and complex separation steps (such as the conventional ion exchange, demineralization, precipitations etc.) are not needed, but generally the xylitol can be purified in a single step chromatographically, whereafter it is crystallized to obtain pure xylitol. Ethanol is easy to remove from the fermentation solution for instance by evaporation. Thus the need for separating xylitol from the hexitols and other sugars produced in the hydrolysis and reduction steps is avoided. The hydrolysis performed in accordance with the invention also provides a solution to the problem of using pulp discarded as waste mass, in other processes, and thus in the process of the invention substantially the entire starting material is utilized.

BRIEF DESCRIPTION OF THE FIGURE

The FIGURE graphically illustrates the results from Example 2 of the application by showing the content of various samples, including xylitol-rich fractions, obtained via chromatographic separation.

DETAILED DESCRIPTION OF THE INVENTION

Almost any xylane-containing material can be used as a starting material in the process of the invention. Possible starting materials include softwood, such as birch, beech, poplar, alder etc., and plants or plant constituents, such as straw or hulls of wheat, corn, oat or barley, corn cobs and stems of corn, nutshells, bagasse, and cottonseed bran. When wood is used as a starting material, it is advantageously comminuted or used as chips, sawdust, etc. and treated by hydrolysis or steam explosion and posthydrolysis, in which connection a carbohydrate material useful in this invention is obtained.

In addition to the above, for instance by-products which are formed in processing and production of woodpulp and which have a high xylane or xylose content can be used. As an example may be mentioned the acid sulphite waste liquor produced in the manufacture of woodpulp by the sulphite process, said waste liquor containing small quantities of undissolved wood solids, and soluble substances such as lignosulphonates, hexoses and pentoses, including xylose, and being a good raw material for use in the production of xylitol. Other by-products and waste products produced in the processing of paper and woodpulp, such as prehydrolysates from the production of viscose mass and waste liquor from the so called neutral sulphite process, which have a high xylane and/or xylose content, can also be used.

The process of the invention employs an aqueous solution containing free xylose. Thus it may be necessary to carry out an acid and/or enzyme hydrolysis on the starting material to break down the xylane into xylose. Processes for hydrolyzing xylane-containing materials to produce xylose-containing solutions have been described e.g. in U.S. Pat. Nos. 3,784,408 (Jaffe et al.) and 3,586,537 (Steiner et al.).

The starting material may, if desired, be pretreated before the fermentation to remove constituents which may be toxic or otherwise disadvantageous to the yeast. The necessity of the pretreatment step is dependent on the starting material used and the yeast used in the fermentation step. The pretreatment of the starting material may include for instance posthydrolysis, chromatographic separation, ion exchange purification, precipitation, etc.

The process chart is as follows:

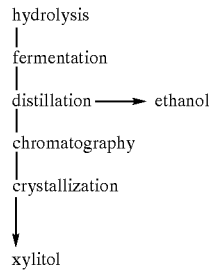

The hydrolysis can comprise two steps, prehydrolysis of the cellulose-containing raw material, which may be effected using the so called steam explosion method, and the enzymatic hydrolysis of the polysaccharides and oligosaccharides to produce the corresponding monosaccharides. This step is carried out using enzymes which have a high cellulolytic and xylanolytic activity.

The remaining solids, consisting for the most part of lignin, are then separated from the solution obtained. Alternatively, said solids and the solids produced in the fermentation, such as yeast, can be separated or collected after the next distillation.

When relatively impure solutions are used as a starting material, pretreatment of the solutions may be necessary in some cases. The pretreatment may be e.g. posthydrolysis and/or separation of the constituents which may be toxic and/or disadvantageous to the yeast employed or which have an adverse effect on the fermentation or separation steps. The pretreatment may also be combined with chromatographic separation, ion exchange purification, precipitation, etc.

Thereafter, the solution is fermented with a suitable yeast strain. The invention employs yeasts that are capable of reducing xylose into xylitol and hexoses into ethanol and/or use hexoses for their growth. Such yeasts are for instance yeasts of the genera *Candida, Pichia, Pachysole* and *Debaryemyces*. *Candida* and *Debaryemyces* species, particularly *Candida tropicalos* and *Debaryemyces hanseii*, are regarded as advantageous. As a good example may be mentioned the *Candida tropicalos* strain deposited at the American Type Culture Collection under the accession number ATCC 9968.

The xylose content of the aqueous solution to be fermented is dependent on the starting material and process steps employed, but is advantageously about 50–300 g/l.

The fermentation can be carried out in most commercially available fermentors which are furnished with aerating means and stirring and pH regulating means. The temperature is advantageously about 20–40° C., most advantageously about 30° C. The yeast cells are added to the xylose-rich solution. Generally, it can be said that the higher the yeast concentration, the faster the fermentation step is. It has been found that the yeast concentration is advantageously about 1–20 g of dry yeast/l of substrate (dry weight) when the xylose content is about 50–300 g/l.

The fermentation can be enhanced by adding nutrients, and it is continued until the most part of the xylose has been converted to xylitol and substantially all hexoses have been converted to ethanol and/or used for yeast growth. The fermentation generally takes about 24–144 hours, preferably 24–72 hours. With the process of the invention, up to 90% of the xylose can be converted to xylitol.

After the fermentation step, the solution is clarified prior to the separation of xylitol and ethanol therefrom. The yeast cells are removed after the fermentation. This may be carried out by centrifugation, filtration or some other similar procedure. When the yeast cells have been removed and the solution is clear, the ethanol produced in the fermentation is recovered by evaporation, distillation or a similar procedure. Alternatively, the removal of the yeast cells can be carried out after the distillation.

To recover xylitol, chromatographic separation is first performed. This is advantageously carried out in a column filled with a sulphonated polystyrene resin cross-linked with divinylbenzene in the alkali/alkaline-earth form. A large-scale chromatographic method suitable for this purpose has been described in U.S. Pat. No. 3,928,193 (Melaja et al.). The chromatographic separation may also be carried out using a simulated mobile bed, as described in U.S. Pat. No. 2,985,589. A DVB cross-linked sulphonated polystyrene resin is used as a filler for the column.

From the fraction having a high xylitol content obtained from the chromatographic step, xylitol can be crystallized with a good yield using conventional crystallization methods, such as cooling or evaporation crystallization. When cooling crystallization is used, xylitol crystals of an average diameter of about 30 μ are added as seed crystals to the concentrated xylitol solution, whereafter the temperature of the solution is slowly decreased. The crystals obtained, the average diameter of which is about 250–600 μ, are separated for instance by centrifugation and washed with water to obtain substantially pure crystalline xylitol.

The process can also be carried out in a preferable alternative way so that the starting material is subjected to partial hydrolysis and extraction. The prehydrolysate obtained from the extraction is then fermented to convert xylose to xylitol, which is separated chromatographically and crystallized in the above-stated manner. A final hydrolysis is carried out on the extracted mass, the hydrolysis product is fermented to convert hexoses to ethanol, and ethanol is recovered in the manner described above.

The invention is described in further detail by means of the following examples, which are not intended to restrict the invention.

EXAMPLE 1

Production of Ethanol and Xylitol from Birch Chips

A steam explosion treatment was carried out on birch chips at 215° C. with a delay time of 4.5 minutes. The apparatus used is commercially available (Stake Technology, Canada).

30 kg of chips pretreated by steam explosion were suspended in 400 l of water at 50° C. in a reactor furnished with stirring means. The pH of the suspension was regulated to 4.8 with a NaOH solution. The following enzymes were added into the reactor:

| | |
|---|---|
| Cellulase Multifect L 250 (Cultor) | 4 FPU/g d.s. |
| Beta-Glucosidase Novozyme 188 (Novo) | 5 IU/g d.s. |
| Hemicellulase Multifect K (Cultor) containing | |
| xylanase | 18 U/g d.s. |
| β-xylosidase | 9 nkat/g d.s. |
| esterase | 2 nkat/g d.s. |

The reaction was started, and after three and six hours pretreated birch chips were added to the mixture to increase the solids content to 14% by weight. The hydrolysis was continued for three days at 50° C. and at a pH of 4.8. The yield after the hydrolysis was 16% of glucose and 12% of xylose on the dry weight of the pretreated chips.

The solution was separated from the dry solids in a decanting centrifuge (Sharples P 600). The finely powdered matter was removed in a Westfalia Na7-06-076 separator, and the xylose-glucose solution was concentrated by evaporation. The pH of the concentrate was 5.1, and the composition was the following:

| | |
|---|---|
| glucose | 10.3% |
| xylose | 7.6% |
| other monosaccharides | 3.1% |
| oligosaccharides | 5.5% |

The total solids content was about 32%.

The solution additionally contained salts of organic acids and small amounts of lignin decomposition products, furfural, phenols and other organic substances.

The hydrolyzed product was fermented with the yeast *Candida tropicalis* ATCC 9968. A New Brunswick Scientific Co If 250 fermentor was used, whereto gas analysis and mass spectrometric apparatus was connected.

The fermentation solution contained:

| | |
|---|---|
| 60 l | prehydrolysate (dry solids content about 32%) |
| 1.5 kg | Gistex yeast extract (steam sterilized at 121° C., 15 min.) |
| 29 l | water |

The inoculation cultures were grown in two stages, first in a 2 l Erlenmeyer flask in an Orbital Shaker at 30° C. for 2 days, and then in a Microgen SF 116 laboratory fermentor having an operating volume of 11 l. The fermentor was aerated at a rate of 5.5 Nl/min. (0.5 VVM) and stirred at a rate of 500 rpm. The culturing lasted for one day.

The actual fermentation was performed on a pilot scale, the operating volume being 100 l. The fermentor was aerated at a rate of 20 Nl/min. (0.2 VVM) and stirred at a rate of 100 rpm. The temperature was maintained at 30° C. and the pH at 6. Plurior® was used as an antifoaming agent.

The fermentation results have been set forth in Table 1.

TABLE 1

| time (h) | yeast (g/kg) | xylitol (g/l) | glucose (g/l) | ethanol (g/l) |
|---|---|---|---|---|
| 0 | 2.0 | 0.0 | 53.5 | 1.9 |
| 16 | 6.1 | 2.9 | 2.4 | 26.4 |
| 23.5 | | 4.7 | | 26.7 |
| 41.0 | 7.4 | 9.0 | 1.9 | 25.6 |
| 65.0 | 8.0 | 15.8 | | 24.9 |
| 91.5 | 6.1 | 21.2 | | 23.4 |
| 136 | | 20.6 | | 22.3 |

After the fermentation, substantially all sugars had converted into xylitol or ethanol.

Ethanol was recovered from the solution by distilling the fermented solution in a conventional manner. The distillation apparatus was constructed of standard components (Corning Process Systems) which were of borosilicate glass, and the apparatus comprised equipment for 15 separation steps as follows: boiler, 13 bubble plates and a feed plate between the fourth and fifth bubble plates seen from the top. The diameter of the column was 10 cm.

The distillation was carried out at a pressure of 110 mbar at a feed rate of 10 l/h and with a reflux ratio of 3:1. 110 l of fermenting solution gave 7.0 kg of distillate which contained 27.1% by weight of ethanol. The ethanol content of the bottom product was 0.02% by weight.

The separation and, if desired, crystallization of xylitol were carried out as described in Examples 2 and 3.

EXAMPLE 2

Production of Ethanol and Xylitol from Sulphite spent Liquor

The starting material used was a sugar fraction chromatographically separated from a sulphite, spent liquor (Finnish Patent Application 862273, U.S. Pat. No. 4,631,129), containing a considerable amount of hexoses, mainly glucose. The composition of the solution prior and subsequent to fermentation is shown in Table 2.

TABLE 2

| Ingredient | before fermentation | after fermentation |
|---|---|---|
| dry solids, % by weight | 19.0 | — |
| oligosacch., g/l of dry solids | 14.8 | 10.3 |
| glucose g/l | 90.0 | 1.4 |
| xylose g/l | 42.0 | 3.5 |
| arabinose g/l | 5.0 | 2.3 |
| xylitol g/l | — | 25.4 |
| ethanol g/l | — | 42.0 |
| arabinitol g/l | — | 2.8 |

The fermenting was carried out with a *Debaryomyces hansenii* strain, and 3 g/l of yeast extract, 3 g/l of malt extract and 5 g/l of peptone were added. The pH of the solution to be fermented was initially about 6.0, the temperature was about 30° C. and the fermentation was carried out in an Orbital Shaker (200 rpm).

The ethanol produced in the fermentation was recovered by distillation (50° C., 200 mbar), and a chromatographic separation was carried out on the remaining solution in a column filled with a divinylbenzene-cross-linked polystyrene-based cation exchanger, in which connection the following conditions were used:

| | |
|---|---|
| height of column | 40 m |
| diameter of column | 22.5 cm |
| temperature | 65° C. |
| flow rate (H$_2$O) | 30 l/h |
| feed concentration | 30 % by weight |
| feed volume | 6 kg of solid matter |
| resin: | |
| Finex C 09 | |
| particle size | 0.37 mm |
| ionic form | Na$^+$ |

The results have been graphically presented in the figure. Xylitol was separated from xylose and the other impurities, and recovered from the xylitol-rich fraction, wherefrom pure xylitol was crystallized in the manner described in Example 3.

EXAMPLE 3

Crystallization of Xylitol

Xylitol was crystallized from a chromatographically enriched xylitol solution containing 82.5% of xylitol on dry solids by evaporating the solution to 92% by weight of dry solids at 65° C. Into a solution of a natural weight of 2 200 g, xylitol crystals of about 0.04 mm were inoculated in an amount of 0.03% by weight, and the solution was cooled in 55 hours to 45° C. in accordance with the following empirical equation:

$$T = T1 - (t/t1)^{**}2^* (T1-T2),$$

wherein
T=temperature of solution, ° C.
T1=seeding temperature (65° C.)
T2=final temperature (45° C.)
t=time from seeding, h
t1=crystallization time (55 h)

The crystallization was carried out in a 2 l pilot crystallizer furnished with a vertical stirrer. 65% of the xylitol present in the solution crystallized as raw crystals which were separated from the mother solution in a basket centrifuge (Hettich, Roto Silenta II).

During the centrifugation, the crystals were washed with water (4% of water on the weight of the crystals). The centrifugation time was 5 minutes, and a centrifugal force of 2 000 g was used. 1 510 g of natural weight of a crystal suspension was centrifuged, which gave 705 g of crystalline dry solids having a xylitol content of 99.4% of dry solids. The average size of the crystals was 0.37 mm and the standard deviation 24%.

The raw crystals can be recrystallized into product crystals by the method disclosed in Finnish Patent 69 296.

EXAMPLE 4

Production of Ethanol and Xylitol from Barley Hulls

Barley hull mass having the following carbohydrate composition was used as a starting material:

| | |
|---|---|
| xylan | 21.6% of dry solids |
| glucan | 33.4 |
| arabinan | 5.7 |
| galactan | 1.4 |
| mannan | 0.6 |
| rhamnan | 0.2 |

The barley hull mass was hydrolyzed at a pressure of 350 psi at 235° C., and the delay time was 2.0 minutes. The hydrolyzed material contained 46.6% of dry solids, and the content of dissolved solids was 34.2% on dry solids. The filtrate contained 12.7% of monosaccharides, 16.9% of acetic acid and 0.5% of furfural calculated on dry solids. Posthydrolysis was carried out on the filtrate by adjusting the pH to 1 with sulphuric acid and by hydrolyzing the solution for 4 hours at a pressure of one atmosphere at 100° C. The composition of the posthydrolysate was the following:

| | | |
|---|---|---|
| oligosaccharides | 1.3% | of dry solids |
| monosaccharides | 45.2%: | |
| xylose | 67.3% | of the |
| arabinose | 11.4% | mono- |
| glucose | 16.0% | sacchar- |
| galactose | 3.3% | ides |
| mannose | 1.5% | |
| rhamnose | 0.5% | |
| others (e.g. furfural) | 3.3% | of dry solids |

The fermentation of the posthydrolysate, the recovery of ethanol and the crystallization of xylitol were carried out as described in the preceding examples.

EXAMPLE 5

Production of Ethanol and Xylitol from Oat Hulls

Oat hull mass having the following carbohydrate composition was used as a starting material:

| | |
|---|---|
| xylan | 26.5% of dry solids |
| glucan | 30.7% |
| arabinan | 3.0% |
| galactan | 1.3% |
| mannan | 0.2% |

The oat hull mass was hydrolyzed at a pressure of 350 psi at 235° C., and the delay time was 2.0 minutes. The hydrolyzed material contained 39.1% of dry solids, and the content of dissolved solids was 36.4% of dry solids. The filtrate contained 12.0% of monosaccharides, saccharides 12.9% of acetic acid and 0.5% of furfural fural calculated on dry solids. Posthydrolysis was performed on the filtrate by adjusting the pH to 1 with sulphuric acid and by hydrolyzing the solution for 4 hours at a pressure of one atmosphere at 100° C. The composition of the posthydrolysate was the following:

| | | |
|---|---|---|
| oligosaccharides | 1.3% | of dry solids |
| monosaccharides | 63.1%: | |
| xylose | 69.0% | of the |
| arabinose | 6.9% | mono- |
| glucose | 19.1% | sacchar |
| galactose | 3.1% | ides |
| mannose | 0.8% | |
| rhamnose | 1.1% | |
| others (e.g. furfural) | 2.8% | of dry solids |

The fermentation of the posthydrolysate, the recovery of ethanol and the crystallization of xylitol were carried out as described in the preceding examples.

EXAMPLE 6

Steam Explosion and Extraction of Birch Chips

A steam explosion treatment was carried out on birch chips with a factory-scale equipment at a temperature of 215° C. with a delay time of 4.5 minutes. The manufacturer of the equipment used is Technip, type of apparatus Stake II System.

The steam explosion product was suspended in hot process water in a mixing container to produce a fibrous suspension of about 3.5%. Therefrom the slurry was directed via an overflow to form a smooth layer on a 5-phase band filter operating on the counter-current principle (type A 40-B25; manufacturer Filters Philippe; width of wire 2.7 m; wire supplied by manufacturer of apparatus). The solid mass was further extracted with hot water on the wire. The aqueous solution obtained had:

| | |
|---|---|
| dry solids content | 8.7% by weight |
| xylose monomers | 1.1% of natural weight |
| xylose oligomers | 3.7% of natural weight |
| glucose | 0.04% of natural weight |

EXAMPLE 7

Enzymatic Degradation of Steam-Exploded Water-Washed Birch Chip Mass

The composition of the steam-exploded (215° C./4.5 min.) birch chip mass (prepared in accordance with Example 6) used as raw material for the hydrolysis was the following:

| | |
|---|---|
| dry solids | 32% |
| cellulose | 60% of dry solids |
| xylan | 3.6% of dry solids |
| lignin (extractable in acetone) | 25% of dry solids |
| Klason lignin | 12.3% of dry solids |

90 kg of the above-described mass was weighed into a reaction vessel provided with a stirrer and a heating jacket and containing 370 l of water. The mixture was heated to 50° C., the pH was adjusted to 4.8–5.0, whereafter the enzyme solutions were added (1.24 l of Multifect L 250, 0.11 l of Novozyme 188 and 0.09 l of Multifect K). As activity units, the added quantities correspond to 6 FPU/g of cellulase, 5 IU/g of β-glucosidase and 0.02 ml of growth solution/g of mass dry solids of hemicellulase (18 U/g of dry solids of xylanase, 9 nkat/g of dry solids of β-xylosidase, 2 nkat/g of dry solids of esterase). The reaction was allowed to continue under the conditions described above for 18 hours. Thereafter mass and enzymes were added in the same quantities as in the starting phase. A corresponding mass and enzyme addition was repeated after 21 hours from the start. Thereafter the hydrolysis reaction was allowed to continue so that the total time was 40 hours. The enzyme action was then stopped by heating the mass mixture to 80° C. for 10–20 minutes. In that connection, the remaining solid matter was solidified and thereby made easier to separate. The solid matter and the solution were separated from one another by centrifugation (Pennvalt Sharples P 600 model). The solution was further clarified by separating the remaining fine precipitate in a separator (Westfalia model NA7-06-076). The solution was concentrated to 33% for fermentation by evaporating with a Luwa evaporator in vacuo at a temperature of 40–50° C.

Hydrolysis yields of steam exploded, water washed birch chip mass in enzyme treatment:

| | % in solution | yield % of dry solids | conversion % |
|---|---|---|---|
| glucose | 3.3 | 24.5 | 40.8 |
| xylose | 0.4 | 2.6 | 72.0 |
| oligosaccharides | 0.7 | | |

Composition of the clarified and evaporated enzyme hydrolysate solution:

| | |
|---|---|
| glucose | 22.7% of natural weight |
| xylose | 2.7% of natural weight |
| oligosaccharides | 4.7% of natural weight |

EXAMPLE 8

Fermentation of Enzymatic Hydrolysate of Steam Exploded, Water Washed Birch Chip Mass into Ethanol The hydrolyzed cellulose was fermented with a yeast *Candida tropicalis* ATCC 9968. A New Brunswick Scientific IF-250 fermentor was used.

The fermentation solution contained:

| | | |
|---|---|---|
| 45 l | hydrolysate | |
| 1.5 kg | Gistex yeast extract | |
| 40 l | water | |

The inoculation cultures were grown in two steps, first in a 2 l Erlenmeyer flask in an Orbital Shaker at 30° C. for 2 days, then in a New Brunswick Scientific SF-116 laboratory fermentor having an operating volume of 11 l. The fermentor was aerated 5.5 Nl/min. (0.5 vvm) and stirred at a rate of 500 rpm. The culturing lasted for one day.

The actual fermentation was carried out on a pilot scale, the operating volume being 100 l. The fermentor was aerated 25 Nl/min (0.25 vvm) and stirred at a rate of 100 rpm. The temperature was adjusted to 30° C., and the foam was controlled with Plurior antifoaming agent.

The results of the fermentation are set forth in Table 4.

TABLE 4

| time (h) | cell mass (g/l) | glucose (g/l) | ethanol (g/l) |
|---|---|---|---|
| 0 | 1.8 | 105.0 | 1.9 |
| 19.5 | 11.3 | 0 | 51.2 |
| 52 | — | 0 | 48.1 |
| 66 | — | 0 | 45.0 |

In the course of 29.5 hours, the yeast consumed all of the glucose in the substrate, producing ethanol therefrom with a yield of 48%.

After fermentation, the yeast cells were separated from the solution by centrifugation (Westfalia NA7-06-076). The clarified solution was distilled to recover the ethanol.

EXAMPLE 9

Recovery of Ethanol from the Fermentation Product of Enzymatic Hydrolysate of Steam Exploded, Water Washed Birch Chip Mass 100 litres of fermented cellulose hydrolysate were distilled. The fermentation had been carried out in the manner described in Example 8 and clarified by centrifugation in a Westfalia NA7-06-076 separator. The ethanol content of the solution was 3.4%.

The distillation apparatus was constructed of standard components by Corning Process Systems which were of borosilicate glass. The diameter of the column was 10 cm. The apparatus comprised 15 separation steps: boiler, 13 bubble plates and a feed plate between the fourth and fifth bubble plates seen from the top. The distillation was carried out at a pressure of 100 mbar, at a feed rate of 10 l/h and with a reflux ratio of 3:1. 8.5 kg of distillate were recovered, having an ethanol content of 36.0%. The ethanol content of the bottom product was 0.1%.

What is claimed is:

1. A process for the simultaneous production of xylitol and ethanol from a hydrolyzed lignocellulose-containing material, comprising
providing a starting material of hydrolyzed lignocellulose-containing material comprising xylose and glucose in aqueous solution, wherein xylose content is 50–300 g/l;
fermenting said starting material with a yeast strain which is capable of converting xylose to xylitol and glucose present to ethanol to form a fermented product comprising xylitol, ethanol and yeast, wherein during fermentation the xylose in the starting material is converted to xylitol and the glucose in the starting material is converted to ethanol and 22.3 g/l to 51.2 g/l of ethanol is produced in the fermentation solution;
recovering the resulting ethanol by distillation of the fermentation solution to obtain a distillate with ethanol and a remaining solution; and
recovering xylitol from the remaining solution by chromatographic separation.

2. The process according to claim 1, wherein lignocellulose-containing material hydrolyzed is birch or grain hulls.

3. The process according to claim 1, further comprising crystallizing pure xylitol.

4. The process according to claim 1, wherein yeast cells are removed prior or subsequent to the distillation.

5. The process according to claim 1 wherein the yeast strain is of the genus *Candida* or *Debaryomyces*.

6. The process according to claim 1, wherein the yeast is *Candida tropicalis*.

7. The process according to claim 1, wherein the yeast is *Debaryomyces hansenii*.

8. The process according to claim 1, wherein the hydrolyzed lignocellulose-containing material is produced by steam explosion and enzymatic hydrolysis of lignocellulose-containing material.

9. The process according to claim 1, wherein the chromatographic separation is carried out with a strong cation-exchanging resin as a stationary phase.

10. The process according to claim 1 wherein the fermentation is carried out at a pH of about 4–7.

11. The process according to claim 6, wherein the yeast is *Candida tropicalis* ATCC 9968.

12. The process according to claim 10, wherein the fermentation is carried out at a pH of about 5.7 and at a temperature of about 25–35° C.

13. The process according to claim 1, wherein the hydrolyzed lignocellulose-containing material is produced by a process selected from the group consisting of acid hydrolysis, enzymatic hydrolysis and a combination thereof.

14. The process according to claim 13, wherein hydrolysis is carried out by acid hydrolysis.

15. The process according to claim 1 wherein the lignocellulose-containing material is treated by steam explosion followed by hydrolysis.

16. The process according to claim 1, wherein the fermentation is carried out at a pH of about 4–7 and at a temperature of about 25–35 C with a yeast concentration of 1 to 20 g per liter of solution for 24–144 hours in the presence of nutrients.

17. A process for the simultaneous production of xylitol and ethanol from a hydrolyzed lignocellulose-containing material, wherein lignocellulose-containing material hydrolyzed is selected from the group consisting of softwood, birch, beech, poplar, alder, plants, plant constituents, straw, hulls of wheat, corn, oat, barley, corn cobs, corn stems, nutshells, bagasse, cottonseed bran, wood chips, sawdust, sulphite spent liquor from woodpulp processing, waste from paper processing, and waste from woodpulp processing, comprising:
providing a starting material of hydrolyzed lignocellulose-containing material comprising xylose and glucose in aqueous solution, wherein xylose content is 50–300 g/l;
fermenting said starting material to produce a fermented solution with a yeast capable of converting xylose present in the starting material to xylitol and glucose present in the starting material to ethanol, said yeast selected from the group consisting of a yeast of the genera *Candida, Pichia, Pachysolen,* and *Debaryomyces*, said fermenting comprising reducing said xylose to xylitol and said glucose to ethanol, and said fermented solution comprising xylitol, ethanol, and spent yeast; wherein during fermentation the xylose in the starting material is converted to xylitol glucose in the starting material is converted to ethanol and 22.3 g/l to 51.2 g/l of ethanol is produced into the fermentation solution;

separating a substantial portion of said spent yeast from said fermented solution to produce a substantially clarified solution comprising ethanol and xylitol, said clarified solution comprising substantially less spent yeast by weight on a dry solids (substance) basis than said spent yeast in said fermented solution, and said separating comprising at least one separating method selected from group consisting of filtration, centrifugation and decanting;

recovering ethanol by distillation to obtain a distillate with ethanol and a remaining solution;

recovering xylitol from the remaining solution by chromatographic separation; and crystallizing said xylitol to produce xylitol crystals.

18. A method according to claim 17 wherein hydrolysis to produce lignocellulose-containing material comprises at least one of the following: i) prehydrolysis of said lignocellulose-containing material by steam explosion of said lignocellulose-containing material and enzymatic hydrolysis of said lignocellulose-containing material with enzymes having a cellulolytic and xylanolytic activity to hydrolyze said lignocellulose-containing material; and ii) acid hydrolysis of said lignocellulose-containing material.

19. A method according to claim 17 including removing solids comprising lignin from said fermented solution.

20. A method according to claim 17 wherein said yeast is selected from the group consisting of *Candida tropicalis* strain having an accession number ATCC 9968, and *Debaryomyces hansenii*.

21. A method according to claim 17 wherein fermenting occurs at a temperature ranging from about 10 to about 45 degrees C at a pH ranging from 4 to 7 with a yeast concentration of about 1 to about 20 g of dry yeast per liter of solution having a xylose content of about 50 to about 300 g/l for about 24 to about 72 hours in the presence of nutrients.

22. A method according to claim 17 wherein said crystallizing is selected from the group consisting of cooling crystallizing and evaporation crystallizing.

23. A method according to claim 17 wherein said xylitol crystals are separated by centrifugation and washed with water to produce substantially pure crystalline xylitol.

24. A method according to claim 17, wherein: said starting material of hydrolyzed lignocellulose-containing material comprising xylose and glucose further comprises arabinose.

* * * * *